United States Patent [19]

Ward et al.

[11] Patent Number: 5,506,300
[45] Date of Patent: Apr. 9, 1996

[54] COMPOSITIONS THAT SOFTEN AT PREDETERMINED TEMPERATURES AND THE METHOD OF MAKING SAME

[75] Inventors: Robert S. Ward, Lafayette; Judy S. Riffle, Oakland, both of Calif.

[73] Assignee: Thoratec Laboratories Corporation, Berkeley, Calif.

[21] Appl. No.: 19,248

[22] Filed: Feb. 18, 1993

Related U.S. Application Data

[63] Continuation of Ser. No. 516,617, Apr. 30, 1990, abandoned, which is a continuation of Ser. No. 918,521, Oct. 10, 1986, abandoned, which is a continuation-in-part of Ser. No. 688,793, Jan. 4, 1985, abandoned.

[51] Int. Cl.$^6$ .......................... C08L 75/06; C08L 75/08; C08L 75/02; C08L 75/04
[52] U.S. Cl. ............... 525/88; 525/54.21; 525/54.22; 525/55; 525/123; 525/177; 525/178; 525/185; 525/416; 525/419; 525/453; 525/454; 525/455; 525/540
[58] Field of Search ................ 525/54.21, 54.22, 525/55, 88, 123, 177, 178, 185, 416, 419, 453, 454, 455, 540

[56] References Cited

U.S. PATENT DOCUMENTS

| | | | |
|---|---|---|---|
| 2,774,745 | 12/1956 | Hedlund | 260/16 |
| 3,384,679 | 5/1968 | Stetz, Jr. | 260/830 |
| 3,619,455 | 11/1971 | Clement | 264/230 |
| 3,699,063 | 10/1972 | Scheibelhoffer | 260/18 TN |
| 3,957,905 | 5/1976 | Sumoto et al. | 260/860 |
| 4,053,548 | 10/1977 | Lundberg | 264/230 |
| 4,085,165 | 4/1978 | Odaka | 260/859 R |
| 4,115,472 | 9/1978 | Porter | 260/836 |
| 4,141,951 | 2/1979 | Beckman | 264/230 |
| 4,168,173 | 9/1979 | Pohl | 96/115 P |
| 4,193,899 | 3/1980 | Brenner | 260/23.5 A |
| 4,210,478 | 7/1980 | Shoney | 156/242 |
| 4,253,893 | 3/1981 | Clinefelter et al. | 156/112 |
| 4,277,391 | 7/1981 | Charles | 260/40 R |
| 4,336,358 | 6/1982 | Alberts | 525/439 |
| 4,448,913 | 5/1984 | Coleman et al. | 523/455 |
| 4,451,605 | 5/1984 | Theodore | 524/423 |
| 4,452,841 | 6/1984 | Oliviera | 428/174 |
| 4,473,671 | 9/1984 | Green | 523/105 |
| 4,485,227 | 11/1984 | Fox | 528/61 |
| 4,496,349 | 1/1985 | Cosentino | 604/175 |
| 4,831,094 | 4/1989 | Stein | 526/283 |

FOREIGN PATENT DOCUMENTS

| | | |
|---|---|---|
| 0101427 | 2/1984 | European Pat. Off. . |
| 0150454 | 12/1984 | European Pat. Off. . |
| 0129396 | 12/1984 | European Pat. Off. . |
| 0182629 | 5/1986 | European Pat. Off. . |
| 2138095 | 12/1972 | France . |
| 0087329 | 1/1983 | France . |
| 2546170 | 5/1984 | France . |
| 53-10875 | 1/1978 | Japan . |
| 58-28096 | 6/1983 | Japan . |
| 59-53528 | 3/1984 | Japan . |
| 59-20541 | 11/1984 | Japan . |
| 60-28433 | 2/1985 | Japan . |
| 1211118 | 11/1970 | United Kingdom . |

OTHER PUBLICATIONS

*The Chemical Dictionary*, 10th Ed., revised by Gessner G. Hawley, Van ostrand Reinhold Co., New York (1981) 797–798.
French Patent No. 2,138,095: Informal English Translation of pp. 1–2 of Description and Claims.
English translation (14 pages) of French Patent No. 2,138, 095.

Primary Examiner—W. Robinson Clark
Attorney, Agent, or Firm—Flehr, Hohbach, Test, Albritton & Herbert

[57] ABSTRACT

The present invention provides a composition that softens at a predetermined temperature, preferably between about 20° C. and 90° C., and more preferably between about 20° C. and about 62° C., comprising at least one block copolymer having at least two thermal transition temperatures. The composition is characterized by at least two thermal transition temperatures, one of which is a predetermined lower transition temperature, preferably between about 20° C. to 90° C., and more preferably between about 20° C. to about 62° C., and one of which is an upper transition temperature. The present invention also provides a method of making the composition, a method of making biomedical materials and articles, and toys and toy components, with shape-memory properties from the composition, and biomedical materials and articles, and toys and toy components, with shape-memory properties made from the composition.

13 Claims, No Drawings

COMPOSITIONS THAT SOFTEN AT PREDETERMINED TEMPERATURES AND THE METHOD OF MAKING SAME

This is a continuation of application Ser. No. 07/516,617, filed Apr. 30, 1990, which is a continuation of application Ser. No. 06/918,521 filed Oct. 10, 1986, which is in turn a continuation-in-part of application Ser. No. 06/688,793, filed Jan. 4, 1985, all of which are now abandoned.

Generally, the present invention relates to a composition that softens at a predetermined or selected temperature, preferably between approximately room temperature and about 90° C., and more preferably between room temperature and approximately 62° C. (about 25° C. above body temperature), but maintains good mechanical integrity well above that softening point, and the method of making said composition. The present invention also relates to biomedical devices and materials and articles with shape-memory properties made from said composition and the method of making said biomedical devices and materials and articles with shape-memory properties.

The composition of the present invention is ideally suited for biomedical uses and is especially suited for catheters. Because catheters are inserted into the body, the ideal catheter should have a high flexural modulus or stiffness similar to that of a hypodermic needle. This is particularly true for intravenous catheters which are inserted through the skin for a short distance and then inserted directly into a blood vessel. Since ease of insertion is a property that is most important in initially placing the catheter, intravenous catheters have always been made from high flexural modulus materials. Once the catheter is in place inside the vein, the stiff property or high flexural modulus is a distinct disadvantage. High flexural modulus can result in irritation of the inner surface of the blood vessel by the tip of the catheter. As a result of the inflammatory irritation to the inside of the blood vessel, it is very common for these catheters to produce blood clots and become infected.

A very soft, rubber-like material would have much less tendency to irritate the inside of the blood vessel and would result in reduced morbidity and increased life of the catheter (the length of time before the catheter has to be replaced or moved to a different site). However, a flexible catheter would lack ease of insertion. Thus, there is a need for a catheter which is both easy to insert and does not irritate the inside of the blood vessel. The ideal catheter composition would have a very high modulus or stiffness upon insertion and would soften once inside the blood vessel.

There are other applications for memory shape materials such as for use in toys. For example, a shape memory material could be used as settable dolls' hair that can be set by a child using water at an appropriate temperature to shape various reversible hair styles. Other uses include action figures that change shape when heated, vehicles in other shapes that can be restored to original condition after a "collision," and the like.

It is an object of the present invention to provide compositions that soften at a predetermined or selected temperature, preferably above approximately room temperature, but maintain good mechanical integrity above that softening point, and the method of making said composition.

It is another object of the present invention to provide biomedical devices and materials that soften at predetermined temperatures between about body temperature (37° C.) and about 62° C. (25° C. above body temperature), and the method of making said biomedical devices and materials.

It is another object of the present invention to provide articles with shape memory properties that soften at predetermined temperatures between about 20° C. and about 90° C., and preferably between about 20° C. and about 62° C., and the method of making said articles.

It is yet another object of the present invention to provide articles for use in toys and other articles with shape memory properties.

In general, the present invention provides a composition that softens at a predetermined temperature, preferably above about 20° C., comprising at least one block copolymer having at least two thermal transition temperatures. The composition has at least two thermal transition temperatures, one of which is a predetermined or selected lower transition temperature, preferably above about 20° C. and one of which is an upper transition temperature, preferably above 90° C., and more preferably above about 62° C. The composition has the physical properties of a rigid, glassy or crystalline polymer below the predetermined transition temperature and the physical properties of a flexible, elastomeric polymer above the predetermined transition temperature, but below the upper transition temperature. In a preferred embodiment, the composition further comprises a plasticizer or polymer that has at least one thermal transition temperature and is thermodynamically compatible with at least one block of the block copolymer and substantially incompatible with at least one block of the copolymer. For most biomedical applications, the composition of the present invention has a predetermined glass transition temperature at or near body temperature. The present invention also provides a method of making the composition and a method of making biomedical devices and materials and articles with shape-memory properties from the composition. The present invention further provides biomedical devices and materials and articles with shape-memory properties made from the composition.

In a first embodiment of the present invention, the composition comprises at least one block or segmented copolymer having a lower thermal transition temperature (either a glass transition temperature (Tg) or a melting point (Tm)) between about 20° C. and about 62° C. and an upper thermal transition temperature (either a Tg or Tm) above about 62° C. A major volume fraction of the block copolymer may have a lower transition temperature between about 20° C. to about 62° C. if a dramatic drop in flexural modulus is desired when the composition passes through the lower transition temperature. In such case, the major volume fraction of the block copolymer must also have the physical properties of a rigid, glassy or crystalline polymer below the lower transition temperature and the physical properties of a flexible, rubbery polymer at and above the lower transition temperature but below the upper transition temperature. However, if a less dramatic drop in flexual modulus is desired, then the block copolymer may have a minor volume fraction (i.e., less than 50%) having the lower transition temperature between about 20° C. and 62° C.

In another embodiment of the present invention, the composition comprises at least one block copolymer and a material that is selected from the group consisting of plasticizers and polymers that are thermodynamically compatible with at least one block of said block copolymer. Other blocks or segments of the block copolymer base are thermodynamically incompatible with the plasticizer or second polymer. The plasticizer or second polymer has at least one thermal transition temperature, (either a Tg or Tm) and the block copolymer base has at least two thermal transition temperatures.

The block copolymer or segmented copolymer is the base polymer of the composition. The plasticizer or second polymer is blended together with the base polymer. The compatible blocks of the base polymer and the plasticizer or second polymer form a miscible blend with a transition temperature between the thermal transition temperature of the compatible block of the base polymer and the thermal transition temperature of the plasticizer or second polymer. The transition temperature of the miscible blend may be varied by varying the relative amounts of the two components. The blocks or segments of the base polymer which are incompatible with the plasticizer or second polymer should have a Tg or Tm higher than the temperature range to be encountered in the end use of the composition of the present invention. The incompatible block of the base polymer will have a Tg or Tm in the composition very close or equal to the Tg or Tm it had in the unblended base polymer.

At temperatures above the predetermined transition temperature of the composition, the blend will be analogous to a thermoplastic elastomer with a soft block transition temperature that may be varied over a wide range of temperatures. The temperature range over which the transition takes place will narrow if the two miscible components are highly compatible, producing an abrupt change in the mechanical, thermal, transport, electrical, and other properties of the blend as the temperature is raised or lowered through the transition temperature.

The properties of the blend at temperatures above and below the predetermined transition temperature can be varied considerably by varying the composition of the base polymer. Greater concentration of the miscible or compatible block in the base polymer will result in a greater proportion of the blend subsequently possessing the predetermined transition temperature of the composition. For instance, in a 60/40 blend of a polycaprolactone(PCL)/ diisocyanatodiphenylmethane(MDI)/butanediol(BD) polyurethane base polymer and phenoxy resin, the soft block, PCL concentration of the base polymer may be varied. At very low PCL concentration, the blend will be very rigid below the predetermined transition temperature and will soften little when heated above the predetermined transition temperature. At high PCL concentration in the base polymer, the blend will soften dramatically above the predetermined transition temperature.

Similarly, the incompatible blocks or segments of the base polymer may be chosen to vary the properties of the blend. A hard block composed of hexamethylene-diisocyanate and butanediol would have a lower transition temperature than a rigid block of diisocyanatodiphenylmethane and butanediol within the range of end use temperatures.

The compatible block or blocks in the base polymer and the second polymer or plasticizer have special requirements relative to each other. In addition to being thermodynamically compatible as determined by a single transition temperature for the blend, the block copolymer (base polymer) and plasticizer or second polymer are selected such that the lower transition temperature (Tg or Tm) of the block copolymer is different than the transition temperature (Tg or Tm) of the plasticizer or second polymer, one of the transition temperatures being higher and one lower than the desired or predetermined transition temperature of the composition. Generally, the compatible block of the base polymer will have the lower Tg or Tm and the second polymer will have the higher Tg or Tm. As the second polymer is added to the base polymer, the Tg or Tm of the soft block or segment of the base polymer increases. However, it is also possible to use a higher Tg or Tm base polymer with two hard blocks, only one of which is compatible with the plasticizer and a lower Tg or Tm plasticizer. As the lower Tg or Tm plasticizer or second polymer is added to the base polymer, the Tg or Tm of the compatible block of the base polymer decreases. In both cases, the relative amount of the second polymer or plasticizer will determine the final Tg or Tm of the compatible block of the base polymer and accordingly, the predetermined thermal transition temperature of the blend.

The composition of the present invention is further characterized by the physical properties of a rigid, glassy, semi-crystalline, or crystalline polymer below the predetermined transition temperature and the physical properties of a soft, elastomeric polymer at and above the predetermined transition temperature, but below the upper transition temperature of the composition. The physical or mechanical properties of glassy or crystalline polymers and rubbery polymers are described in "Mechanical Properties of Polymers and Composites, " L. E. Nielsen, Dekker, N.Y. (1974), and "Properties of Polymers, Their Estimation and Correlation with Chemical Structure," D. W. Van . Krevelen, Elsevier, N.Y. (1976), and are well known to those skilled in the art.

For biomedical uses, a preferred embodiment of the composition of the present invention has a predetermined glass transition temperature between about body temperature and about 62° C. For certain biomedical applications, such as making catheters, drug release devices, or thermal indicators, a preferred embodiment of the composition has a glass transition temperature at or near body temperature.

Accordingly, for certain biomedical applications, a preferred embodiment of the composition of the present invention is characterized by the physical properties of a rigid, glassy or crystalline polymer in the dry state at a temperature below about body temperature (preferably at a temperature between about 25°–35° C. or below) and is characterized by the physical properties of a flexible, rubbery polymer in the hydrated state at about body temperature to the next transition temperature which should be above at least about 50° C., preferably above about 62° C.

For biomedical applications, a preferred composition of the present invention comprises at least one block copolymer and a second polymer thermodynamically compatible with at least one block of said block copolymer, wherein the block copolymer is characterized by at least two thermal transition temperatures, one being below about body temperature and the other being well above body temperature, preferably above about 62° C. The second polymer has at least one transition temperature (either a Tg or Tm) above body temperature.

For application as softenable, shape memory polymers in toys, the preferred composition of the present invention comprises a base polymer comprising a block polyester-polyether copolymer. The two thermal transition temperatures of such polymers will be determined, and thus can be controlled somewhat by the respective molecular weights and by the relative amounts of soft segments and hard segments but will primarily be determined by the specific hard (polyester) segments and soft (polyether) blocks present in the polyester-polyether. Block polyester-polyether copolymers may have glass transition (TG) temperatures at about −50° C. and a well defined melting point (Tm) up to about 200° C.

The block copolymer (base polymer) is selected from the group consisting of polyester urethanes, polyether urethanes, polyurethane/ureas, polyether-polyamides, polyether-polyesters, and any other block or segmented copolymers containing at least one polyether or polyester block or segment. One preferred block copolymer (base polymer) is a polyester urethane. Polyester urethanes have glass transition temperatures of about −50° C. to −10° C. and about 100° C. to 150° C. Another preferred block copolymer is a polyether urethane. Polyether urethanes have glass transition temperatures of about −85° C. to −40° C. and about 100° C. to 150° C.

A particularly preferred class of block copolymers (particularly for use in toys) is the class of block copolymers comprising polytetramethylene or polypropylene glycol terephthalate soft segments and polybutyleneterephthalate or polyethylene terephthalate hard segments. A class of polyesterpolyether block copolymers are commercially available under the trade name Hytrel® (DuPont) and are available in varying amounts of soft segments/hard segment ratios. A typical Hytrel® block copolymer containing 42% polytetramethylene ether glycol terephthalate soft segment and 58% 1,4-butanediol terephthalate hard segments will have a Tg of the amorphous phase at about −50° C. and well defined melting point (Tm) of the crystalline phase at about 200° C.

The second polymer is preferably selected from the group consisting of polyvinylchloride, styrene/acrylonitrile copolymers, polyhydroxyethers, polycarbonates, polyesters, polyethers, nitrocellulose, cellulose derivatives, and polystyrene. A preferred second polymer is the polyhydroxyether of bisphenol-A and epichlorohydrin (phenoxy resin). The phenoxy resin has a glass transition temperature of about 91° C.

The two polymers are then blended in a ratio so that the predetermined lower transition temperature for the composition will be at or near body temperature or slightly above body temperature if hydration lowers this glass transition temperature further.

When used for catheters or other biomedical applications, the composition of the present invention may also contain a minor amount of a surface modifying additive. The surface modifying additive reduces the coefficient of friction and increases blood compatibility of the composition. In addition, radiopaque fillers may be used in the composition to render the catheters visible by fluoroscopy. Surface modifying additives may be selected from the group consisting of block multipolymers containing polysiloxanes or polyfluorocarbons as one block. Preferred surface modifiers are selected from the group consisting of polysiloxane/polyester block copolymers and polysiloxane/polyurethane copolymers. A more preferred surface modifier is a polysiloxane/polyester block copolymer. Radiopaque fillers may be selected from the group consisting of barium sulphate, bismuth subcarbonate, bismuth oxychloride, tantalum and other non-corrosive metals. A preferred radiopaque filler is barium sulphate.

Although the composition of the present invention has many biomedical applications, a preferred use for the composition is for catheters. For use as a catheter, a preferred embodiment of the composition has a glass transition temperature at or near body temperature, such that when the composition is at room temperature, it is below its glass transition temperature and is stiff and rigid, having the physical properties of a glassy or crystalline polymer. Accordingly, a catheter made of the composition will be easy to insert through the skin and into the blood vessel. As the composition warms to body temperature, it will go through the transition and its flexural modulus will be decreased dramatically by as much as one to three orders of magnitude, causing the composition to soften considerably. Thus, while in the blood vessel the catheter will have less tendency to irritate the inside of the blood vessel and thus, less tendency to cause blood clots and become infected.

Because most intravenous catheters have thin walls, they have a tendency to heat up very quickly when exposed to a new elevated temperature. As a result, the catheter can actually begin to soften as it is being inserted into the body, making insertion difficult. Therefore, a more preferred embodiment of the composition of the present invention has a predetermined lower thermal transition temperature slightly above body temperature. When the catheter is inserted into the body, the composition absorbs water from the blood and becomes plasticized; its predetermined lower transition temperature is lowered from slightly above body temperature to just below body temperature. The composition then goes through its transition to become a rubbery, flexible solid.

Another use for the composition of the present invention is for making contact lenses that soften at or near body temperature in the hydrated state. At room temperature, the composition would have a high flexural modulus and therefore could easily be machined into lenses. Once put in place in the eye, the composition would heat up, absorb water, pass through its predetermined lower transition temperature and become soft, flexible, and comfortable for the wearer and more permeable to gases, such as oxygen and carbon dioxide.

For other biomedical applications, a preferred embodiment of the composition of the present invention will have a predetermined lower transition temperature above body temperature but below about 62° C. and an upper transition temperature above about 62° C., such that the composition has the physical properties of a rigid, glassy or crystalline polymer at about body temperature and the physical properties of a flexible, rubbery polymer at about 10° C. above body temperature to just below the upper transition temperature.

An example of a biomedical use for this preferred embodiment of the composition of the present invention is for making a material for constructing casts for broken limbs. The composition can be formed into a biomedical tape or sock which can be softened by warming it to its predetermined lower transition temperature in hot or warm water or with a heat gun. When it becomes soft and flexible, it can be used to wrap or encase a broken limb that has Just been set. As the material cools to room temperature, it goes through the lower transition and becomes virtually as rigid as Plaster of Paris. The material remains rigid at body temperature to at least bathing temperature. The composition may replace Plaster of Paris as a material for constructing casts. The shape memory properties of the material can be used in this application to cause a prestretched sock to shrink around the limb when heated.

Another use for the composition of the present invention is for making articles with shape-memory properties that change shapes at a predetermined transition temperature in the range of about 25° C. to about 62° C. For example, the composition can be heated to a temperature close to or above its upper transition temperature, oriented under stress into a specific shape (configuration #1) then cooled while in that configuration #1 to below the lower predetermined or selected transition temperature of the composition. The composition can be cold formed into another shape (configuration #2) at that temperature, or the composition can be heated above its lower transition temperature but below its upper transition temperature and then cooled to below its lower transition temperature while being constrained in another shape (configuration 2). When the composition is heated to a temperature above the lower predetermined transition temperature but below the upper transition temperature while unrestrained, it will spontaneously reassume configuration #1.

Thus, for instance, a catheter with shape-memory properties could be made from the composition of the present invention. The composition could be formed into a catheter in one configuration above its upper transition temperature then cooled to below a lower transition temperature at or near body temperature and formed into a second configuration (e.g., a straight configuration). Upon insertion into the body, the catheter would warm to body temperature (above its lower glass transition temperature) and reassume its first configuration.

Another use for the composition of the present invention would be for the production of toys with shape-memory properties. The composition could be extruded, molded or oriented under stress into one toy shape above the composition's upper transition temperature. When cooled below the predetermined lower transition temperature, the toy could be reshaped by children. Then, the toy could be warmed to above its predetermined lower transition temperature, thus reassuming its original shape.

Another use for compositions of the present invention is to prepare specific products for use in toys, such as settable dolls' hair. The preferred compositions for this particular use are those having a Hytrel® base polymer and previously-described phenoxy resin (a polyhydroxyether of bisphenol-A and epichlorohydrin) as the second polymer. Exemplary blends include mixtures of 40D Hytrel® (67% soft segment), 55D Hytrel® (42% soft segment) and 63D Hytrel® (24% soft segment), respectively, with the aforementioned phenoxyresin. When made into fibers, these blends are useful as dolls' hair which is settable at or above 40° C.

Other uses for the polyester-polyether block copolymers for use as toys include action figures which change shape when heated, vehicles and other shapes that can be restored to original condition after a "collision", configured shapes such as sheets that can be molded or otherwise shaped at low temperatures by a child into various reversible constructions, plastic baked goods that rise when heated in a toy "oven", toy snakes that coil or unwind in warm water, and the like.

The present invention also contemplates the method of making a composition that softens at a predetermined temperature. One embodiment of the method of the present invention comprises the steps of selecting the desired thermal transition temperature and then preparing a block copolymer that has at least two thermal transition temperatures, one of said transition temperatures being a lower transition temperature equal to the predetermined or selected transition temperature of the composition and the second transition temperature being well above that transition temperature. For most uses, a major volume fraction of the block copolymer should have a transition temperature equal to the predetermined lower transition temperature for the composition in order to achieve the desired degree of softening as the composition passes through the predetermined lower thermal transition temperature. Preferably, the predetermined lower transition temperature of the composition is in the range of about 20° C. (near room temperature) to about 62° C. (about 25° C. above body temperature) and the upper transition temperature is above about 62° C.

For biomedical applications, it is preferred that the predetermined lower transition temperature of the composition be between about body temperature (37° C.) and about 62° C. For catheters and similar biomedical devices inserted into the body, it is preferred that the predetermined lower transition temperature of the composition be at or near body temperature.

The various blocks or segments of the block copolymer are selected such that the physical properties of the composition are that of a rigid, glassy or crystalline polymer below the predetermined lower transition temperature of the composition and that of a flexible, rubbery polymer at and above the lower transition temperature, but below the upper transition temperature.

The block copolymer selected for use in the composition of the present invention can be made by a method described in: 1. J. A. Moore, ed., *Macromolecular Syntheses*, Collective Vol. 1, John Wiley and Sons, N.Y., (1977), p. 79, 381. 2. J. H. Saunders, and K. C. Frisch, eds., *Polyurethanes, Chemistry and Technology, Vol. 1, Chemistry*, Interscience Div. of John Wiley and Sons, N.Y., (1962). 3. W. R. Sorenson and T. W. Campbell, *Preparation Methods in Polymer Chemistry*, Interscience Div. of John Wiley and Sons, N.Y., (1961).

Polyester-polyether block copolymers may be prepared by methods known in the art. See, for example, *Handbook of Thermoplastic Elastomers*, Walker, B. M., ed., Van Nostrand-Rheinhold (1979). The preferred Hytrel® copolymers discussed above may be prepared and are characterized as described in the paper entitled "High Performance Thermoplastic Elastomer", D. F. Brizzolara, presented at the American Chemical Society Rubber Division, Los Angeles, California,. Apr. 23–27 (1985).

A second embodiment of the method of the present invention comprises the steps of selecting the desired transition temperature for the composition, selecting or making a block copolymer such that said block copolymer has at least two thermal transition temperatures. The lower transition temperature of the block copolymer should be either above or below the predetermined or selected lower transition temperature of the composition. A plasticizer or second polymer that is thermodynamically compatible with at least one block of the block copolymer and that has at least one thermal transition temperature (either a Tg or Tm) that is either above or below the predetermined transition temperature of the composition is selected or prepared, then blended together with the block copolymer such that the lower thermal transition temperature of the block copolymer and the thermal transition temperature of the compatible plasticizer or second polymer combine to form the predetermined lower transition temperature of the composition. The plasticizer selected for use in the composition of the present invention can be made by the method described in W. R. Sorenson and T. W. Campbell, *Preparative Methods in Polymer Chemistry*, Interscience Div. of John Wiley and Sons, N.Y., (1961), and G. Odian, *Principles of Polymerization*, McGraw-Hill, N.Y. (1970). The second polymer selected for use in the composition of the present invention can be made by the method described in W. F. Hale, *Encyclopedia of Polymer Science and Technology*, 10, 111 (1969), and H. Lee, D. Stoffey, and K. Neville, *New Linear Polymers*, McGraw-Hill, N.Y., (1967).

For biomedical uses, a surface modifier and/or a radiopaque filler can be blended together with the block copolymer in the first embodiment of the method of the present invention or with the base polymer and thermo-dynamically compatible plasticizer or second polymer in the second embodiment of the method.

Extending and reinforcing fillers that are not radiopaque may be used in nonbiomedical or biomedical applications and, in some instances, may enhance shape memory properties.

The present invention also contemplates a method of making biomedical devices or materials that soften at a predetermined or selected temperature between about body temperature and about 62° C. In most applications, the predetermined softening temperature will be at or near body temperature. The method comprises the steps of making the composition of the present invention by either of the method embodiments discussed above, then forming it into a biomedical device or material. The composition of the present invention can be formed into a catheter, a drug release device, a thermal indicator, biomedical tape for constructing casts for broken limbs, contact lenses or many other biomedical devices.

The present invention is also directed to the biomedical devices or materials that soften at a predetermined temperature between about body temperature and about 62° C. made by the method of the present invention or made with the composition of the present invention.

The present invention also provides a method of making articles with shape memory properties that soften at a predetermined temperature in the range of about 25° C. to about 62° C., comprising the steps of making the composition of the present invention, heating said composition to a temperature above said composition's upper transition temperature, orienting said composition under stress into a first configuration, cooling said composition to below the predetermined lower transition temperature while said composition is in said first configuration, and then cold forming said composition into a second configuration. The present invention also provides articles with shape-memory properties made according to the foregoing method or made from the composition of the present invention.

The following table indicates the decreasing flexural modulus of a preferred composition of the present invention for biomedical uses when it comprises various ratios of phenoxy resin and polyester urethane:

| Phenoxy Resin/ Polyester Urethane | Flexural Modulus [psi] | | |
|---|---|---|---|
| Wt/Wt | 23° C. Dry | 37° C. Dry | 37° C. Hydrated |
| 60/40 | 186400 | 159000 | 6729 |
| 50/50 | 160400 | 8950 | 602 |
| 40/60 | 93300 | 2867 | 1186 |

The flexural modulus data in the column designated "37° C. Hydrated" was obtained by measuring the composition's flexural modulus after one hour of hydration in 37° C. distilled water. The flexural modulus data in the two columns designated "Dry" was obtained by measuring the composition in its dry state at the designated temperatures. The following examples describe the tests from which this data was obtained and the preferred compositions of the present invention.

EXAMPLE 1

A composition of the present invention comprising 60 weight percent of a resin comprised of the polyhydroxyether derived from bisphenol-A and epichlorohydrin (phenoxy resin) and 40 weight percent of a commercial polyester urethane (Estane 5707 produced by B. F. Goodrich), in the form of compression molded sheets, was measured for flexural modulus in a thermal mechanical analyzer at 23° C., 37° C. and at 37° C. after an hour of hydration in distilled water. The flexural modulus of the composition at 23° C. was 186,400. The flexural modulus at 37° C. was 159,000 and the flexural modulus after one hour of hydration in 37° C. distilled water was 6,729.

EXAMPLE 2

A composition of the present invention comprising 50 weight percent of the phenoxy resin described in Example 1 and 50 weight percent of the polyester urethane described in Example 1, in the form of compression molded sheets, was measured for flexural modulus in a thermal mechanical analyzer. At 23° C., the composition had a flexural modulus of 160,400. At 37° C., the composition had a flexural modulus of 8,950 and after one hour of hydration in 37° C. distilled water, the composition had a flexural modulus of 602.

Transition temperatures of each blend component separately and of the final composition were measured by differential scanning calorimetry (DSC) as follows:

| | |
|---|---|
| Phenoxy resin: | Tg = 91° C. |
| Polyester urethane: | Tg = −19° C. |
| Blend (50% phenoxy resin/50% Estane 5707): | Tg = 39° C. |

Additionally, 40 weight percent of the phenoxy resin, 40 weight percent of the polyester urethane, and 20 weight percent of a polysiloxane-polycaprolactone block copolymer surface modifier (36 weight percent polysiloxane) were melt blended. The transition near body temperature of that composition as measured by DSC was Tg=27° C.

EXAMPLE 3

The composition of the present invention comprising 40 weight percent of the phenoxy resin described in Example 1 and 60 weight percent of the polyester urethane described in Example 1, in the form of compression molded sheets, was measured for flexural modulus in a thermal mechanical analyzer. At 23° C., the composition had a flexural modulus of 93,300. At 37° C., the composition had a flexural modulus of 2,867 and after one hour of hydration in 37° C. distilled water, the composition had a flexural modulus of 1186.

EXAMPLE 4

The composition of the present invention comprising 50 weight percent of the phenoxy resin described in Example 1 and 50 weight percent of a commercial polyether-based polyurethane (Estane 5714 produced by B. F. Goodrich) were melt blended and the transition temperatures were measured by differential scanning calorimetry (DSC) as follows:

| | |
|---|---|
| Phenoxy resin: | Tg = 91° C. |
| Polyether-based polyurethane: | Tg = −48° C. |
| Blend (50% phenoxy resin/ 50% polyurethane): | Tg = 22° C. |

Additionally, 40 weight percent of the phenoxy resin, 40 weight percent of the polyether-based polyurethane, and 20 weight percent of a polydimethylsiloxane-polycaprolactone block copolymer surface modifier (36 weight percent polysiloxane) were melt blended. The transition temperature occurring around but below body temperature as measured by DSC was Tg=5° C. This result indicates that the selected surface modifier is thermodynamically compatible with the base polymer and the second polymer. Less surface modifier should be used to achieve a final Tg near 22° C. Typically for biomedical applications, about 0.5 weight percent of a surface modifier would be used.

Examples 5 through 7 illustrate the control of the lower transition temperature of softenable, shape-memory blends by varying the relative amount of polyester-polyether base polymer and phenoxy anti-plasticizer. By employing different polyesterpolyether hardnesses/compositions, phenoxy content can be chosen to produce identical Tg values in blends having a range of physical properties. Examples 7 through 9 demonstrate the latter technique. Example 11 further illustrates the tailoring of physical properties with constant (40° C.) lower transition for the case of dolls' hair. Example 12 demonstrates various manifestations of shape-memory exhibited by the polyester-polyether blends.

EXAMPLE 5

The glass transition temperature (Tg) can be varied by preparing blends containing different volume fractions of the Hytrel® polyester-polyether and phenoxy. In this example blends were prepared by varying the amount of Hytrel® 40D, (67% soft segment) and the phenoxy. Pellets of each material were dried prior to use. The appropriate amounts of each material were weighed, placed in a sealed container, and tumble blended in order,to achieve a uniform mixture. A conical twin-screw extruder was used to combine the polymers in the melt. The extrudate was pelletized on line and several 2–3 foot sections of rod were collected, Compression molded sheets were prepared from the pellets and used for determining thermal and physical properties, The rods were used to demonstrate the shape-memory properties of the Hytrel® 40D/Phenoxy blends.

Four blends with different Hytrel® 40D/Phenoxy ratios were prepared, A Differential Scanning Calorimeter was used to measure the Tg of the blends, The data listed below shows that the Tg can be varied by changing the Hytrel 40D/Phenoxy ratio,

| Hytrel ® 40D (%) | Phenoxy (%) | Tg (°C.) |
| --- | --- | --- |
| 30 | 70 | 48 |
| 35 | 65 | 40 |
| 38 | 62 | 35 |
| 50 | 50 | 20 |

EXAMPLE 6

The experimental approach in Example 5 was repeated except the materials were prepared by varying the Hytrel® 55D/Phenoxy ratio. The Hytrel® 55D material contains 42% soft segment,

| Hytrel ® 55D (%) | Phenoxy (%) | Tg (°C.) |
| --- | --- | --- |
| 30 | 70 | 57 |
| 41 | 59 | 41 |
| 46 | 54 | 37 |
| 50 | 50 | 33 |

EXAMPLE 7

The experimental approach used in Example 5 was repeated except the materials were prepared by varying the Hytrel® 63D/Phenoxy ratio. The Hytrel® 63D material contains 24% soft segment.

| Hytrel ® 63D (%) | Phenoxy (%) | Tg (°C.) |
| --- | --- | --- |
| 50 | 50 | 44 |
| 53.5 | 46.5 | 39 |
| 63 | 37 | 34 |
| 70 | 30 | 29 |

EXAMPLE 8

Another approach to preparing materials with shape-memory properties is to have the Tg remain constant and vary the type of Hytrel® polyester-polyether. This would result in a series of materials with the same Tg, but with different physical/mechanical properties. In this example a blend of Hytrel® 40D/Phenoxy (35/65) was prepared in the manner described in Example 5. This blend had a Tg of 40° C. with the following physical properties:

| | |
| --- | --- |
| Initial Modulus: | 115000 psi |
| Tensile Strength: | 6100 psi |
| Ultimate Elongation: | 120% |

EXAMPLE 9

In this example a blend of Hytrel® 55D/Phenoxy (41/59) was prepared in the manner described in Example 8. This blend had a Tg of 41° C. with the following physical properties:

| | |
| --- | --- |
| Initial Modulus: | 65700 psi |
| Tensile Strength: | 7200 psi |
| Ultimate Elongation: | 223% |

EXAMPLE 10

In this example a blend of Hytrel® 63D/Phenoxy (53.5/46.5) was prepared in the manner described in Example 8. This blend had a Tg of 30° C. with the following physical properties:

| | |
| --- | --- |
| Initial Modulus: | 99300 psi |
| Tensile Strength: | 7300 psi |
| Ultimate Elongation: | 246% |

EXAMPLE 11

The Hytrel®/Phenoxy blends from Examples 8 through 10 were extruded into fine denier fiber, 4–6 mils outside diameter. The application of this fiber would be for use as settable dolls' hair. In this particular application several factors have to be balanced: the shape-memory property, the glass transition temperature (Tg), physical properties, and the fiber must "feel" like hair. The shape-memory property is important so that the child can repeatedly "set" the doll's hair. The temperature at which this phenomenon occurs (Tg) must be above room temperature, but not high enough to injure the child. The fiber must have sufficient strength so that the toy manufacturer can use existing production equipment to root the fiber into the doll's head. When the fiber is in the final product it should have the feel and drape of the more commony used doll's hair fibers in use today. With all these stipulations in mind, the fibers were prepared from the materials in Examples 8 through 10 because they have a TG around 40° C. The physical properties of the fiber were measured.

| Hytrel® | 40D | 55D | 63D |
| --- | --- | --- | --- |
| Initial Modulus (psi) | 138595 | 155483 | 118021 |
| Tensile Strength (psi) | 12700 | 13200 | 16300 |
| Ultimate Elongation (psi) | 320 | 490 | 488 |

EXAMPLE 12

The shape-memory property of the Hytrel®/Phenoxy blends is demonstrated several ways. In all compositions containing Hytrel® as the base polymer, the upper transition (a $T_m$ of about 200° C.), was unchanged by the presence of phenoxy resin. This indicates the incompatibility of the phenoxy resin with the hard segment of the Hytrel®.

(1) Coil to Straight: A straight extruded rod of the shape-memory material is heated above its lower Tg, wrapped around a cylinder and cooled. The coil is removed from the cylinder. The rod will remain in the coiled form until it is heated. Upon rebating above the lower transition temperature the coil will unwind into a straight rod.

(2) Straight to Coil: A straight extruded rod of the shape-memory material is heated above its lower Tg, wrapped around a cylinder and cooled. The coil remains on the cylinder and is held in place and heated above the upper transition temperature(95° C.) in an oven for about 15 minutes. Heating at lower temperatures (or even no heating) will accomplish the same result, but a longer period of heating will be required. The cylinder is removed from the oven and allowed to cool below its upper transition temperature. The coil is removed from the cylinder. The permanent shape (configuration 1) of the rod is now a coil. The coil is heated above the lower transition and drawn into a straight rod and cooled. The temporary shape (configuration 2) is now a straight rod. Upon reheating above the lower transition temperature the straight rod will transform its shape into a coil.

(3) Shrinking Tube: Extruded tubes are heated above the lower transition temperature and are drawn so that the diameter of the tube is decreased by 60% and the length of the tube is increased, the tube is then cooled to below the lower transition temperature. Upon reheating above the lower transition temperature the diameter increases to 98% of its original diameter and the length of the tube shortens. This is an example of shape-memory in the radial and longitudinal directions.

(4) Kinking Tube: Extruded tubing from the shape-memory materials can be kinked at temperatures below their lower transition temperature. The tubing will hold the kink. When it is heated above its lower transition temperature the tubing will become round again and the kink will disappear. This shape-memory application is important in biomedical catheters, when the doctor or nurse may accidentally kink the catheter during insertion into the patient. If the lower transition temperature is set at body temperature, then the kinked catheter will return to its unkinked shape in a few minutes after it is in the body. Kinked catheters without the shape-memory properties must be removed from the patient and discarded, and a new one must be inserted.

What is claimed is:

1. An article with shape-memory properties made by a method comprising the steps of heating a composition comprising at least one block copolymer and a polymer or plasticizer,
   (i) said polymer or plasticizer being selected from the group consisting of polyvinylchloride, styreneacrylonitrile copolymers, polyhydroxyethers, polycarbonates, polyesters, polyethers, nitrocellulose, cellulose and polystyrene and being thermodynamically compatible with at least one block of said block copolymer and having at least one thermal transition temperature;
   (ii) said blocks of said block copolymer being selected from the group consisting of polyester urethanes, polyether urethanes, polyurethane/ureas, polyetherpolyamides and polyetherpolyesters;
   (iii) said composition being characterized by at least two thermal transition temperatures, one of said transition temperatures being a predetermined lower transition temperature in the range of about 20° C. to about 62° C., the other of said transition temperatures being an upper transition temperature above about 62° C., said composition being further characterized by being rigid below said predetermined lower transition temperature and by being flexible at and above said predetermined lower transition temperature but below said upper transition temperature,
to a temperature above said upper transition temperature, orienting said composition under stress into a first configuration, cooling said composition to below said predetermined lower transition temperature while said composition is in said first configuration, and cold forming said composition into a second configuration.

2. The article according to claim 1 comprising a toy or component of a toy.

3. The toy component according to claim 2 comprising doll hair.

4. The toy according to claim 2 comprising a doll.

5. An article with shape-memory properties made by a method comprising the steps of heating a composition comprising at least one block copolymer and a polymer,
   (i) said polymer being selected from the group consisting of polyvinylchloride, styreneacrylonitrile copolymers, polyhydroxyethers, polycarbonates, polyesters, polyethers, nitrocellulose, cellulose and polystyrene, being thermodynamically compatible with at least one block of said block copolymer and having at least one glass transition temperature;
   (ii) said blocks of said block copolymer being selected from the group consisting of polyester urethanes, polyether urethanes, polyurethane/ureas, polyetherpolyamides and polyetherpolyesters and having a lower glass transition temperature and upper glass transition temperature or melting point;
   (iii) said composition being characterized by at least two thermal transition temperatures, one of said transition temperatures being a predetermined lower glass transition temperature, said predetermined lower composition glass transition temperature being between said lower block copolymer glass transition temperature and said polymer glass transition temperature, the other of said composition transition temperatures being an upper composition glass transition temperature or melting point, said composition being further characterized by being rigid below said predetermined lower composition glass transition temperature and by being flexible at and above said predetermined lower composition glass transition temperature but below said upper composition glass transition temperature or melting point, to a temperature above said upper composition glass transition temperature or melting point, oftenting said composition under stress into a first configuration, cooling said composition to below said predetermined lower glass composition transition temperature while said composition is in said first configuration, and cold forming into a second configuration.

6. The article according to claim 5 comprising a toy or a component of a toy.

7. The toy component according to claim 6 comprising doll hair.

8. The toy according to claim 6 comprising a doll.

9. An article with shape-memory properties made by a method comprising the steps of heating a composition comprising at least one block copolymer and a phenoxy resin, (i) said blocks of said block copolymer being selected from the group consisting of polyetherpolyamides and polyetherpolyesters, and having a lower glass transition temperature and an upper glass transition temperature or melting point;

(ii) said phenoxy resin having at least one glass transition temperature and being thermodynamically compatible with at least one block of said block copolymer;

(iii) said composition being characterized by at least two thermal transition temperatures, one of said transition temperatures being a predetermined lower composition glass transition temperature in the range of about 20° C. to about 62° C., said predetermined lower composition glass transition temperature being between said lower block copolymer glass transition temperature and said phenoxy resin glass transition temperature, the other of said composition transition temperatures being an upper coinposition glass transition temperature or melting point such that said composition is further characterized by being rigid below said predetermined lower composition glass transition temperature and by being flexible at and above said predetermined lower composition glass transition temperature but below said upper composition glass transition temperature or melting point, to a temperature above said upper composition glass transition temperature or melting point, orienting said composition under stress into a first configuration, cooling said composition to below said predetermined lower composition transition temperature while said composition is in said first configuration, and cold forming into a second configuration.

10. The article according to claim 9 comprising a toy or a component of a toy.

11. The toy component of claim 10 comprising doll hair.

12. The toy according to claim 10 comprising a doll.

13. The doll according to claim 12 comprising an action figure.

\* \* \* \* \*